US008506976B2

(12) United States Patent
Tranchant et al.

(10) Patent No.: US 8,506,976 B2
(45) Date of Patent: Aug. 13, 2013

(54) MAKEUP COMPOSITION COMPRISING ENCAPSULATED CARBON BLACK

(75) Inventors: Jean-Francois Tranchant, Marigny les Usages (FR); Myriam Chevalier, Boigny sur Bionne (FR); Emilie Gombart, Orleans (FR)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 13/429,895

(22) Filed: Mar. 26, 2012

(65) Prior Publication Data

US 2012/0251599 A1    Oct. 4, 2012

(30) Foreign Application Priority Data

Mar. 31, 2011    (FR) .................................... 11 52764

(51) Int. Cl.
*A61K 8/02*    (2006.01)
*A61K 8/81*    (2006.01)
*A61K 8/00*    (2006.01)
*A61K 8/11*    (2006.01)
*A01N 59/00*    (2006.01)

(52) U.S. Cl.
USPC .............. 424/401; 424/70.7; 424/64; 424/61; 424/63; 424/125

(58) Field of Classification Search
USPC .................. 424/401, 70.7, 64, 61, 63, 125
See application file for complete search history.

(56) References Cited

U.S. PATENT DOCUMENTS

| | | | |
|---|---|---|---|
| 5,520,917 A * | 5/1996 | Mizuguchi et al. ........... | 424/401 |
| 6,528,568 B2 | 3/2003 | Kinniard et al. | |
| 2006/0283352 A1 * | 12/2006 | Yokoi et al. .................. | 106/31.6 |
| 2007/0134180 A1 | 6/2007 | Simard et al. | |

FOREIGN PATENT DOCUMENTS

| | | |
|---|---|---|
| EP | 0 581 651 | 2/1994 |
| EP | 1 666 544 | 6/2006 |
| EP | 2 025 364 | 2/2009 |
| JP | 60 081012 | 5/1985 |

* cited by examiner

*Primary Examiner* — Aradhana Sasan
(74) *Attorney, Agent, or Firm* — Hamre, Shumann, Mueller & Larson, P.C.

(57) ABSTRACT

The present invention relates to cosmetic make-up compositions, in particular mascaras, comprising carbon black encapsulated in a spherical silica matrix. These compositions are characterized by a deep and glossy black color.

11 Claims, 1 Drawing Sheet

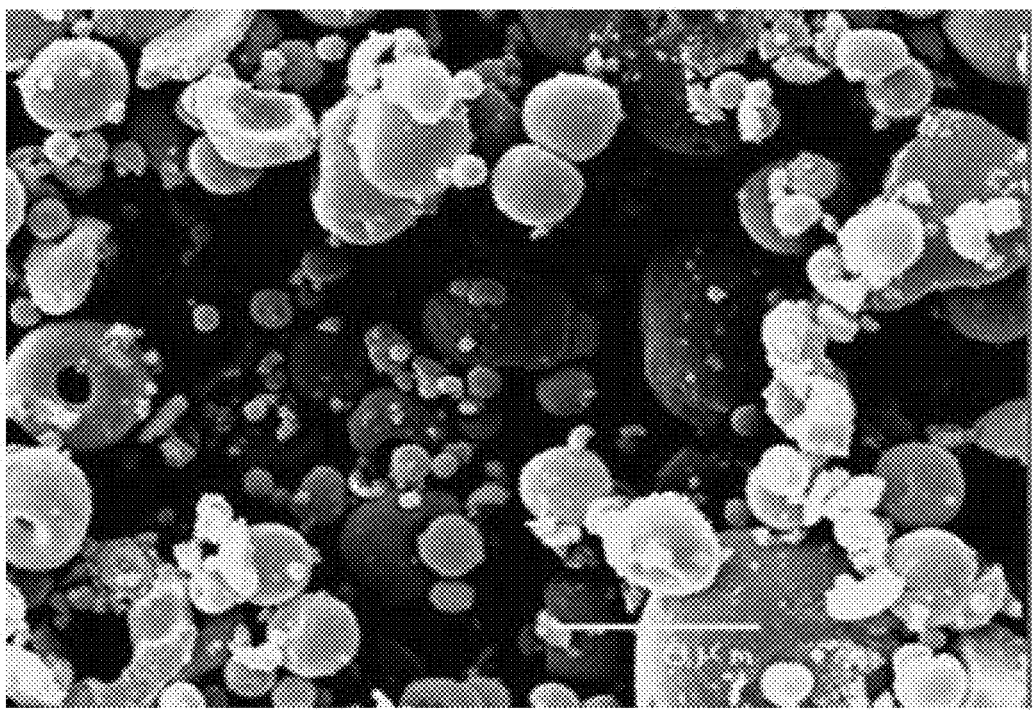

MAKEUP COMPOSITION COMPRISING ENCAPSULATED CARBON BLACK

The invention relates to coloured or colouring cosmetic compositions comprising a black pigment which are intended in particular for making up the skin, eyelashes, eyebrows or nails.

STATE OF THE ART

Pigments are commonly used in industry as insoluble colouring agent in numerous coloured or colouring compositions (paints, inks, make-up products). They are normally incorporated in these compositions in the pulverulent form or dispersed in bases or binders which will fix the pigment to the surface of the support on which these compositions will be applied.

The development of new pigments is a major problem for numerous industries, including the cosmetics industry. The latter is looking more particularly for pigments which produce a superior visual effect as regards the intensity of the tints or colours, or the gloss, in order to incorporate them, for example, in make-up compositions applied to the skin, lips, nails or keratinous fibres, such as the eyelashes or eyebrows.

The colour produced visually by a pigment comes from its ability to absorb a portion of the visible spectrum of light, the wavelengths of which spectrum are approximately between 400 and 700 nm, and to transmit the nonabsorbed wavelengths (complementary spectrum) perceived by the eye.

In order to improve the visual effect produced by the primary pigments, recourse may be had to various treatments targeted, for example, at enhancing the intensity of the tints or colours thereof, or their gloss. Reference is made to treated pigments.

Among the known treatments, it is, for example, possible to coat a substrate using one or more layers of pigments.

Another solution consists in coating the pigment itself using a composition intended to improve the visual effect, such as that taught by U.S. Pat. No. 6,528,568 or Application WO 99/13010.

Application EP 1 666 544 (Nippon Sheet Glass) discloses a pigment provided in the form of shiny black specks comprising a black pigment dispersed in a material of silica or alumina type. The treatment applied makes it possible to obtain specks for which the value of luminosity (or Lightness) L* (according to the CIELAB 1976 model) increases after treatment when this value is compared with that obtained for the primary pigment, which reflects a black colour with a lower intensity than for the primary pigment. This is because, according to the CIELAB model, the lower the value of luminosity L*, the more intense the black, "perfect" black (complete absorption of the light) having the value 0.

The suggestion has also been made, in Application EP 581 651, to increase the luminosity of the tint of pigments by coating them with a porous matrix, in particular a porous silica matrix.

PURPOSES OF THE INVENTION

The present invention is targeted first of all at providing cosmetic compositions which exhibit an improved visual effect and which are intended in particular for making up the skin, lips, nails and/or keratinous fibres. These compositions comprise a pigment with a black colour which is more intense than that of the black pigments of the prior art as illustrated by Application EP 1 666 544 and than that of untreated commercial pigments (primary, pigments).

A further purpose of the invention is to solve the technical problems in a reliable and reproducible way which can be used on the industrial scale, in particular in cosmetics.

BRIEF DESCRIPTION OF THE DRAWING

The FIGURE is a micrograph showing the pigment product obtained in an example described below.

DESCRIPTION OF THE INVENTION

The problems set out above are solved by the present invention. This is because the inventors have now discovered that the incorporation, in a cosmetic composition, of a treated pigment provided in the form of substantially spherical particles formed of an amorphous silica (silicon dioxide) matrix encapsulating carbon black power makes it possible to obtain a particularly noteworthy visual effect which is reflected by a black colour of lower luminosity and a highly satisfactory gloss.

The invention is thus targeted at a cosmetic composition comprising substantially spherical particles formed of an amorphous silica (silicon dioxide) matrix encapsulating carbon black powder. According to a preferred embodiment, the particles are dispersed in a translucent or transparent cosmetic base as such a base makes it possible to optimally display the visual effect provided by the particles.

The term "carbon black" includes carbon black in the pure state or any black pigment essentially composed of carbon black, i.e. at least 90% and better still at least 95% by weight of carbon black. The term "primary pigment" is also used with reference to the absence of treatment of this pigment.

The carbon black used for the invention is preferably a finely divided powder, the mean diameter of which, defined by its $D_{50}$ value, is less than 1 μm.

The black colour thus defined reflects absorption by the pigment of light throughout the visible spectrum, which is reflected experimentally by a characteristic absence of reflection peak in the visible spectrum, when a spectrophotometric measurement is carried out in the range of the wavelengths between 400 nm and 700 nm.

The substantially spherical shape of the particles based on amorphous silica confers, on this black pigment, properties such that it produces an unexpected visual effect in the compositions in which it is incorporated. Specifically, the latter exhibit a depth of colour and a gloss which are superior to those which are obtained by the incorporation of other black pigments, in particular untreated pigments.

Spherical particles is understood to mean particles of substantially spherical shape which in particular do not form specks or needles. A spherical shape is understood to mean a spherical or ovoid shape which can exhibit structural defects, in particular surface defects, such as hollows and/or bumps. The particles can thus comprise concave parts, indeed even, for some particles, be of toric shape. The particles of substantially spherical shape can be regarded as being of spherical shape overall after visualization on a photograph or an equivalent.

"Substantially spherical particles" is understood to mean in particular particles which exhibit a width/length ratio of less than 3 and preferably of approximately equal to 1.

Particles according to the present invention are illustrated in FIG. 1. This definition of the particles of the invention does not exclude the presence of particles having different shapes, in particular when these particles are particles with a substantially smaller size, that is to say, in general, at most half the mean size of the particles regarded as spherical. Typically, spherical particles are amorphous silica beads.

The inventors of the present invention have demonstrated that a treated pigment, obtained by encapsulation of nanometric primary particles of carbon black in an amorphous silica matrix, makes it possible to obtain spherical particles for which the black colour produced is both deeper but also glossier, in particular when it is incorporated in translucent or transparent cosmetic composition bases.

The encapsulation of the primary carbon particles makes it possible in addition to overcome a major disadvantage of this primary pigment. This is because its particle size, of the order of a few nanometers or tens of nanometers, makes the use thereof problematic in compositions intended to be applied to the skin of the human body, as is the case for cosmetic compositions and more particularly make-up compositions, which are applied to the skin, lips, nails or keratinous fibres.

The encapsulation of the carbon particles in amorphous silica matrices makes it possible to significantly increase the final particle size of the pigment of the invention, which makes the use thereof risk-free in the above-mentioned compositions.

The cosmetic composition of the invention is intended in particular for making up the skin, lips, nails or keratinous fibres, such as the eyelashes or eyebrows. It is preferably in the form of a mascara.

Once it is incorporated in coloured or colouring compositions, the pigment of the invention makes it possible to obtain a composition with a visually deeper black (lower values of luminosity L* when they are compared with those obtained for the same compositions comprising another black pigment) and with a higher gloss.

The particles of this pigment of the invention have a size (particle size) significantly greater than that of the primary carbon black particles.

The particles of pigment of the invention exhibit a size, defined by a mean diameter $D_{50}$, preferably of between 0.1 and 200 microns (µm), preferably between 1 and 100 microns and more preferably between 5 and 50 microns, as measured by laser diffraction.

The particles of pigment used for the present invention are advantageously prepared according to a sol-gel process, the use of which, by simple polymerization of precursors in solution, avoids resorting to melting.

Livage (*Revue Verre*, Vol. 6, No. 5, October 2000) describes the encapsulation of chromophores treated by a sol-gel process for the preparation of materials for optical applications, according to which process the organic molecule is dissolved in the solution of precursor alkoxide. The addition of water brings about the hydrolysis and the condensation of the alkoxide, while the organic molecule remains trapped in the silica network which has formed around it.

Typically, a process for the preparation of the particles of pigment as described above comprises a stage in, which a colloid solution (also known as "sol") is formed by dispersing a silica precursor, such as an alkoxysilane, in an aqueous medium. A silica gel is thus obtained.

The precursors commonly used in sol-gel processes of this type are, for example, tetramethoxysilane of formula $Si(OCH_3)_4$ or tetraethoxysilane of formula $Si(OC_2H_5)_4$.

The medium in which the precursors are dispersed is typically an aqueous medium preferably comprising an alcohol advantageously having from 1 to 5 carbon atoms and preferably ethanol.

Preferably, the aqueous medium is composed of a mixture of water and an alcohol having from 1 to 5 carbon atoms, preferably ethanol, the water representing from 10 to 90% by volume of the mixture, preferably from 80 to 85% by volume.

In an additional stage of the preparation process, the carbon black is added to a medium for the formation of a sol or colloidal solution.

The carbon black is generally incorporated in a proportion of between 3 and 90% by weight, with respect to the weight of the pigment of the invention, and preferably between 8 and 60%. Preference is given to a proportion of between 10 and 45% by weight, with respect to the weight of the pigment of the invention.

Once the silica gel comprising the silica and the primary carbon black has been prepared, drying is carried out at ambient temperature by a process which makes it possible to densify the gel following the removal of the solvent and to obtain substantially spherical particles. This drying is advantageously carried out in an oven under mild conditions in order to make possible the formation of spherical particles. Such a process makes possible the formation of droplets of uniform size.

The particles are subjected to a stage of consolidation of the spherical particles by heating at a temperature typically of between 100 and 200° C. for a period of time appropriate for making possible the consolidation of the spherical particles and the production of the pigment used in the invention.

The particles of pigment of the invention are used as colouring fillers in various cosmetic compositions.

Typically, the pigment of the invention is dispersed in a medium suitable for the preparation of coloured and/or colouring compositions.

Another subject-matter of the invention is thus a cosmetic composition comprising particles of pigment according to the invention dispersed in a cosmetically acceptable medium comprising one or more cosmetic excipients.

Advantageously, the composition of the invention comprises the pigment of the invention as defined above dispersed in a cosmetically acceptable medium. According to a preferred embodiment, the composition of the invention can comprise other pigments, whether treated or untreated.

Such a composition is in particular a composition for making up the skin, lips, nails or else keratinous fibres, such as the eyelashes or eyebrows.

The pigment according to the invention exhibits an excellent ability to be dispersed (dispersibility) in pulverulent, liquid, semi-liquid, or pasty media.

The pigment of the invention which is dispersed in such a medium produces, at the time of the application of the composition, a deeper black with a higher gloss, in particular when this composition forms a film.

Although this pigment produces the most noteworthy visual effect when it is incorporated in a translucent or transparent base, such as a mascara or a lipstick, it is also possible to incorporate it in compositions for which the base is rendered opaque by the presence of cosmetic excipients, such as waxes or titanium dioxide. Although the visual effect is less spectacular, the colouring power and the covering power of this pigment are sufficient to make it possible to produce a black colour having a lower luminosity.

It is thus possible to prepare numerous compositions, in particular cosmetic compositions for colouring the skin, lips, nails or keratinous fibres.

The invention thus covers compositions for making up the skin, lips, nails or keratinous fibres, such as the eyelashes or eyebrows.

According to a preferred use, the cosmetic composition comprises from 1 to 99% by weight, advantageously from 1 to 80% by weight and more preferably from 3 to 70% by weight of the pigment of the invention, with respect to the total weight of the composition, the balance being composed of the cosmetically acceptable medium.

The cosmetically acceptable medium in which the pigment of the invention is dispersed advantageously comprises one or more cosmetic excipients advantageously chosen from dispersing agents, preservatives, antioxidants, fragrances, rheology agents, texturing agents, polymers or surfactants.

The polymers can advantageously be chosen for their ability to form a film at the time of their application and, in this case, are advantageously combined with plasticizing agents capable of improving the mechanical properties (elasticity, strength) of the film formed at the time of application of the composition comprising the pigment of the invention.

The composition of the invention can comprise at least one film-forming agent advantageously chosen from polymers known to a person skilled in the art.

The medium can be an aqueous or hydrophilic medium or else can be formed of a fatty phase formed of lipophilic or liposoluble compounds.

The medium in which the pigment of the invention is dispersed can also comprise an immiscible phase and can then be provided in the form of a water-in-oil or oil-in-water emulsion.

Depending on the composition under consideration, the medium can be solid and in particular pulverulent, pasty, liquid or semi-liquid.

As explained above, the cosmetically acceptable medium (also known as "base" in the present patent application) is advantageously transparent or translucent and more advantageously still transparent.

The cosmetic compositions as defined above can also comprise one or more cosmetic active agents chosen in particular from moisturizing agents or humectants, anti-ageing agents, antimicrobial agents or else UV-screening agents.

The cosmetic composition of the invention is advantageously a mascara, a nail varnish, a lipstick, a gloss, an eyeliner, a foundation or an eye-shadow.

According to a preferred use of the invention, the make-up composition is a mascara which, once applied to keratinous fibres, produces a visually deeper black colour and a greater gloss.

The mascara is advantageously formed of a dispersion of particles of the pigment of the invention in a transparent film-forming base.

According to an advantageous use, the mascara advantageously comprises up to 20% by weight of the pigment of the invention as defined above.

Another subject-matter of the invention is targeted at a method for making up the skin, lips, nails or keratinous fibres, such as the eyelashes or eyebrows, characterized in that it comprises the application of a cosmetic composition as defined above in order to obtain an effect of making up the skin, lips, nails or keratinous fibres.

The present invention thus also relates to a cosmetic article for making up the skin, lips, nails or keratinous fibres and more particularly a mascara, said article comprising a composition as defined above or below.

The application of said composition advantageously makes it possible to apply a film of said composition to the part of the body concerned.

The mascara is more particularly applied to the eyelashes or eyebrows using a device of "applicator" type which makes possible a homogeneous application of the composition, so that, after drying of the composition, the film formed is homogeneous and produces the desired visual effect.

The invention also relates to a cosmetic make-up or care method comprising the application, to the skin, of a coloured or colouring cosmetic composition as defined or of a cosmetic article as defined above or below.

Other aims, characteristics and advantages of the invention will become clearly apparent to a person skilled in the art by the result of reading the explanatory description, which refers to the examples which are given solely by way of illustration and which thus cannot in any way limit the scope of the invention.

The examples form an integral part of the present invention and thus have a general scope.

Furthermore, in the examples, all percentages are given by weight, unless otherwise indicated, the temperature is expressed in degrees Celsius, and the pressure is atmospheric pressure, unless otherwise indicated.

EXAMPLES

Example 1

Preparation of Spherical Particles Encapsulating Carbon Black 670 g of colloidal silica (Silicadol 30A—Nippon Chemical Industrial Co. Ltd) were dispersed in 600 ml of an ethanol/water (10/50 v/v) aqueous/alcoholic solution.

The primary carbon black (supplier LCW Sensient), the particle size of which is less than 100 nm, was added to a colloidal silica suspension prepared previously in a proportion of 30% by weight of primary pigment with respect to the weight of colloidal silica. The mixture was homogenized in order to obtain a silica sol comprising the dispersed pigment.

The gel obtained was dried at ambient temperature, under conditions which make it possible to form and densify spherical particles. The particles obtained were subsequently subjected to a consolidation stage (200° C. for 2 hours).

The pigment obtained was provided in the form of spherical particles of amorphous silica encapsulating the carbon black (FIG. 1).

Measurement of L* According to the CIELAB System for Particles

Use was made of the "1976 CIE L*a*b*" (CIELAB) model for representation of colours, in which L* represents the luminosity (or lightness), which makes up the "black-white" colorimetric axis on a scale ranging from the value 0 (black) to the value 100 (white).

The value of L* was measured from the intensity of light received at an angle of 15° with respect to the specular of an incident light beam oriented at 45° with respect to the horizontal plane and shining on a sample of the pigment of the invention or of a composition incorporating said pigment.

The colorimetric measurement was carried out with an MA 98 spectrocolourimeter from X-Rite.

The L* values were obtained under an illuminant D65 10°. A flash unit captured reflection values at the 15° angle value.

Each of the pigments tested, including the pigment of the invention, was compacted in a pot with a thickness of 1 mm.

The L*(15° values obtained for each of the pots are presented in Table 1 below:

| Pigment | L* |
|---|---|
| Particles (70% silica, 30% carbon black) | 9.2 |
| Carbon black | 10.8 |

-continued

| Pigment | L* |
|---|---|
| Iron oxide | 19.6 |
| Titanium oxide | 20.5 |

Surprisingly, the pot containing the pigment of the invention (Example 1) exhibits the lowest L* value, whereas the pigment contains only the equivalent of 30% by weight of carbon black (70% silica), in contrast to the other pots, which contain 100% of primary pigment.

The encapsulation of carbon black in a spherical matrix of amorphous silica makes it possible to obtain a black colour which is more intense and deeper than that obtained for the primary pigments.

Measurement of The Gloss of The Particles (SRR Gloss Test)

The SRR Gloss ("Reflectance Ratio Gloss") test corresponds to Standard ASTM E429-78, "Test Method for Measurement and Calculation of Reflecting Characteristics of Metallic Surfaces Using Integrating Sphere Instruments" (www.astm.org).

This test makes it possible to evaluate the gloss at the surface of a sample by carrying out reflectance measurements, including or excluding the specular.

The spectrocolourimeter is calibrated with the specular excluded and included.

A measurement is carried out on the pot in which the tested pigment occurs (same sample as for the measurement of L*), with the value of the SSR Gloss, calculated by the software of the device using the following formula:

$$((avgTs-avgDs)/avgTs)*100$$

being displayed.

This formula takes into account the mean values for reflectance, specular included (avgTs), and for diffuse reflectance (specular excluded) (avgDs) obtained for each sample.

Specular included (avgTs): all of the energy reflected is taken into account.

Specular excluded (avgDs): the energy reflected at the specular angle is excluded from the measurement of the mean reflectance value.

The measurements are carried out on a Color 15 spectrocolourimeter from GreytagMacbeth, under an illuminant D65 10° with an opening of 10 mm.

The SRR Gloss values obtained for each sample of pigment tested (in-pot measurements) are shown in table 2 below:

| Pigment | SRR Gloss |
|---|---|
| Particles (30% carbon black) | 15.4 |
| Carbon black | 13.6 |
| Iron oxide | 5.1 |
| Titanium oxide | 4.6 |

The pigment of the invention exhibits the highest gloss for the SRR Gloss test, which reflects a gloss effect which is visually superior to that produced by the other primary pigments tested according to the same protocol.

Example 2

Mascara Comprising Particles of Carbon Black Encapsulated in Amorphous Silica

A mascara was prepared existing in the form of a transparent base in which the pigment prepared according to Example 1 has been dispersed.

The mascara has the following formulation (% by weight):

| | |
|---|---|
| Black pigment | 12 |
| 1,3-Butylene glycol | 10 |
| Glycerol | 20.5 |
| Film-forming acrylic polymer (Covavryl ® E14) | 12 |
| Phenoxyethanol | 0.5 |
| Mica | 9 |
| Water | 36 |

The preparation of this composition was reproduced, the pigment of Example 1 being replaced with a reference black pigment (primary carbon black, iron oxide or titanium oxide) according to the same percentage (12% by weight of the composition).

The L* value was calculated according to the same methodology as in Example 1, the mascara composition being compressed into pots.

The L* values obtained for each of the compositions prepared are mentioned in Table 3 below:

| Type of pigment dispersed in the mascara | L* |
|---|---|
| Particles (30% carbon black) | 20.5 |
| Primary carbon black | 21.2 |
| Iron oxide | 21.1 |
| Titanium oxide | 22.7 |

The mascara composition comprising the pigment of the invention exhibits the lowest in-pot L* value. The black produced by this mascara is the deepest, whereas the pigment itself comprises only 30% of primarycarbon black.

The application as a film to the eyelashes of the mascara formed by a transparent base in which the pigment of invention is dispersed produces a more intense visual effect, both with regard to the intensity of the colour and the gloss.

Example 3

Composition for the Lips Comprising Particles of Carbon Black Encapsulated in Amorphous Silica The composition is provided in the form of a stick of lipstick and comprises the pigment of the invention (Example 1) dispersed in a transparent base, such as described in Patent Application FR 10 52411.

The composition has the following formulation (% by weight):

| | |
|---|---|
| Black pigment of the invention | 5.5 |
| Polymer of ATPA * type | 16.5 |
| Ethylhexyl hydroxystearate | 12 |
| Hydrogenated polyisobutene | 55 |
| Cetyl alcohol | 3.2 |
| Styrene/methylstyrene/indene hydrogenated copolymer | 7 |
| Dibutyl lauroyl glutamide | 0.8 |

* INCI = Bis-Dioctadecylamide Dimer Dilinoleic Acid/Ethylenediamine Copolymer.

The composition is formed of an anhydrous transparent base in which the pigment of the invention is dispersed. The base comprises a polymer of ATPA type which structures the lipophilic compounds of the base so as to form a coloured composition in the form of a stick for application to the lips.

Example 4

Mascara Comprising Particles of Carbon Black Encapsulated in Amorphous Silica The mascara below is formed of an opaque base emulsified in water. The formulation thereof is as follows (% by weight):

| | |
|---|---|
| Black pigment of the invention | 15 |
| Paraffin | 17 |
| Hydroxyethylcellulose | 1.3 |
| Gum arabic | 1.7 |
| Triethanolamine | 2.2 |
| Palmitic acid | 2.2 |
| Stearic acid | 2.2 |
| Bis-diglyceryl polyacyladipate-2 | 2.3 |
| $C_{18-36}$ Triglycerides | 3.0 |
| Waxes | 4.5 |
| Preservatives | 2.0 |
| Purified water | qs |

The mascara, once applied as a film to the eyelashes using an applicator, forms a film of an intense and covering black.

The invention claimed is:

1. A cosmetic composition comprising substantially spherical particles of pigment comprising an amorphous silica matrix in which carbon black is encapsulated,
   wherein the particles exhibit a width/length ratio of less than 3,
   wherein the particles are formed by dispersing an alkoxysilane in an aqueous medium composed of a mixture of water and an alcohol having from 1 to 5 carbon atoms, and
   wherein the particles are dispersed in a cosmetically acceptable translucent or transparent medium.

2. The composition according to claim 1, wherein the width/length ratio is equal to 1.

3. The composition according to claim 1, that is a mascara or a lipstick.

4. The composition according to claim 1, wherein the carbon black represents between 10 and 45% by weight of the weight of the particles.

5. The composition according to claim 1, wherein the particles of pigment exhibit a size, defined by a mean diameter $D_{50}$, is between 0.1 and 200 microns.

6. The composition according to claim 1, comprising from 3 to 70% by weight of the pigment, with respect to the total weight of the composition, the balance being composed of the cosmetically acceptable medium.

7. The composition according to claim 1, comprising at least one film-forming agent.

8. A cosmetic article for making up the skin, lips, nails or keratinous fibres, said article comprising a composition as defined in claim 1.

9. A cosmetic make-up or care method, comprising the application, to the skin, lips, nails or keratinous fibres, of a coloured or colouring cosmetic composition as defined in claim 1.

10. The composition according to claim 1, wherein the aqueous medium comprises 80 to 85% by volume of water.

11. The cosmetic article of claim 8, wherein the cosmetic article is a mascara.

* * * * *